United States Patent
Charles et al.

(10) Patent No.: US 10,376,328 B2
(45) Date of Patent: Aug. 13, 2019

(54) SURGICAL PROBE WITH AN INTEGRATED MOTION SENSOR

(71) Applicant: Novartis AG, Basel (CH)

(72) Inventors: Steven T. Charles, Memphis, TN (US); Tammo Heeren, Aliso Viejo, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/681,878

(22) Filed: Aug. 21, 2017

(65) Prior Publication Data

US 2018/0055592 A1    Mar. 1, 2018

Related U.S. Application Data

(60) Provisional application No. 62/379,318, filed on Aug. 25, 2016.

(51) Int. Cl.
| | |
|---|---|
| *A61B 3/10* | (2006.01) |
| *A61B 17/00* | (2006.01) |
| *A61B 34/00* | (2016.01) |
| *A61B 34/20* | (2016.01) |
| *A61F 9/007* | (2006.01) |
| *A61F 9/008* | (2006.01) |
| *A61F 9/009* | (2006.01) |

(52) U.S. Cl.
CPC .............. *A61B 34/77* (2016.02); *A61F 9/009* (2013.01); *A61F 9/00727* (2013.01); *A61F 9/00736* (2013.01); *A61F 9/00821* (2013.01); *A61B 3/1005* (2013.01); *A61B 34/71* (2016.02); *A61B 2017/00075* (2013.01); *A61B 2034/2048* (2016.02); *A61F 2009/00874* (2013.01)

(58) Field of Classification Search
CPC ....... A61B 3/1005; A61B 34/71; A61B 34/77; A61B 2017/00075; A61B 2034/2048; A61F 9/00727; A61F 9/00736; A61F 9/00821; A61F 9/009; A61F 2009/00874
See application file for complete search history.

(56) References Cited

U.S. PATENT DOCUMENTS

| | | | | |
|---|---|---|---|---|
| 2002/0013572 | A1* | 1/2002 | Berlin | A61F 2/14 606/4 |
| 2005/0277802 | A1* | 12/2005 | Larsen | A61N 5/1017 600/1 |
| 2007/0137058 | A1* | 6/2007 | Liu | G01B 3/008 33/561 |
| 2007/0265606 | A1* | 11/2007 | DeBenedictis | A61B 18/20 606/15 |
| 2008/0262484 | A1* | 10/2008 | Hawkins | A61B 18/203 606/12 |
| 2012/0143182 | A1* | 6/2012 | Ullrich | A61B 18/1445 606/45 |
| 2013/0158582 | A1* | 6/2013 | Underwood | A61F 9/00763 606/171 |

(Continued)

*Primary Examiner* — Jocelin C Tanner

(57) ABSTRACT

A surgical probe system comprising a surgical probe having an instrument tip, and at least one motion sensor located within the surgical probe that measures movement and orientation data. The system further includes a processor that is configured to determine movement and orientation of the instrument tip based on the movement and orientation data, and adjust at least one surgical parameter of the surgical probe based on the movement and orientation of the instrument tip to affect a predetermined surgical outcome.

22 Claims, 4 Drawing Sheets

(56) References Cited

U.S. PATENT DOCUMENTS

| | | | |
|---|---|---|---|
| 2014/0171797 A1* | 6/2014 | Hershey | A61B 8/56 600/437 |
| 2015/0148615 A1 | 5/2015 | Brennan et al. | |
| 2015/0148836 A1 | 5/2015 | Heeren | |
| 2016/0051164 A1* | 2/2016 | Derichs | A61B 5/05 600/409 |

* cited by examiner

SURGICAL PROBE WITH AN INTEGRATED MOTION SENSOR

PRIORITY CLAIM

This application claims the benefit of priority of U.S. Provisional Patent Application Ser. No. 62/379,318 titled "SURGICAL PROBE WITH AN INTEGRATED MOTION SENSOR", filed on Aug. 25, 2016, whose inventors are Steven T. Charles and Tammo Heeren, which is hereby incorporated by reference in its entirety as though fully and completely set forth herein.

BACKGROUND

In ophthalmic surgery, a surgeon may typically use surgical apparatus comprising a vitreoretinal system with posterior segment and anterior segment procedure capabilities. The surgical apparatus may also include various probes, an ophthalmic microscope, an endoilluminator, a console with processors and a touch panel screen, and an embedded laser that's controlled from a system screen on the monitor.

The types of probes used may include vitrectomy probes and laser probes. Vitrectomy probes may be used during vitreoretinal surgery to remove ocular tissues, such as vitreous humor and membranes covering the retina. These probes have a port for drawing in and dissecting tissues. The port opens a fixed amount, tissue is drawn into the port utilizing vacuum, the port closes repeatedly, severing the tissue, and the tissue is aspirated. This action may be repeated to remove desired tissues. Surgeons currently need to actively manage cutting rate, aspiration level of flow rate, and positioning of the vitrectomy probe. For example, during large amplitude or rapid movements, aspiration should be reduced to avoid tearing of tissues.

A laser probe may a continuous laser beam or a pulsed laser beam. During ophthalmic surgery, the surgeon must move the laser probe in a constant-velocity fashion to achieve equal burns. For a pulsed laser application, the surgeon needs to stop motion of the laser probe motion to create a circular burn.

BRIEF SUMMARY

The exemplary embodiments provide methods and systems for a surgical probe system comprising a surgical probe having an instrument tip, and at least one motion sensor located within the surgical probe that measures movement and orientation data. The system further includes a processor that is configured to determine movement and orientation of the instrument tip based on the movement and orientation data, and adjust at least one surgical parameter of the surgical probe based on the movement and orientation of the instrument tip to affect a predetermined surgical outcome.

Currently, surgical hand tools are not known to have motion sensors, such as gyros and accelerometers, and thus adjusting surgical parameters are not achieved automatically. Accordingly, advantages of the exemplary embodiments may include reduced iatrogenic tissue damage, such as retinal tears or overly intense laser burns, during ophthalmic surgery.

DETAILED DESCRIPTION

The exemplary embodiment relates to a surgical probe having an integrated motion sensor. The following description is presented to enable one of ordinary skill in the art to make and use the invention and is provided in the context of a patent application and its requirements. Various modifications to the exemplary embodiments and the generic principles and features described herein will be readily apparent. The exemplary embodiments are mainly described in terms of particular methods and systems provided in particular implementations. However, the methods and systems will operate effectively in other implementations. Phrases such as "exemplary embodiment", "one embodiment" and "another embodiment" may refer to the same or different embodiments. The embodiments will be described with respect to systems and/or devices having certain components. However, the systems and/or devices may include more or less components than those shown, and variations in the arrangement and type of the components may be made without departing from the scope of the disclosure. The exemplary embodiments will also be described in the context of particular methods having certain steps. However, the method and system operate effectively for other methods having different and/or additional steps and steps in different orders that are not inconsistent with the exemplary embodiments. Thus, the present disclosure is not intended to be limited to the embodiments shown, but is to be accorded the widest scope consistent with the principles and features described herein.

Figure 1A:
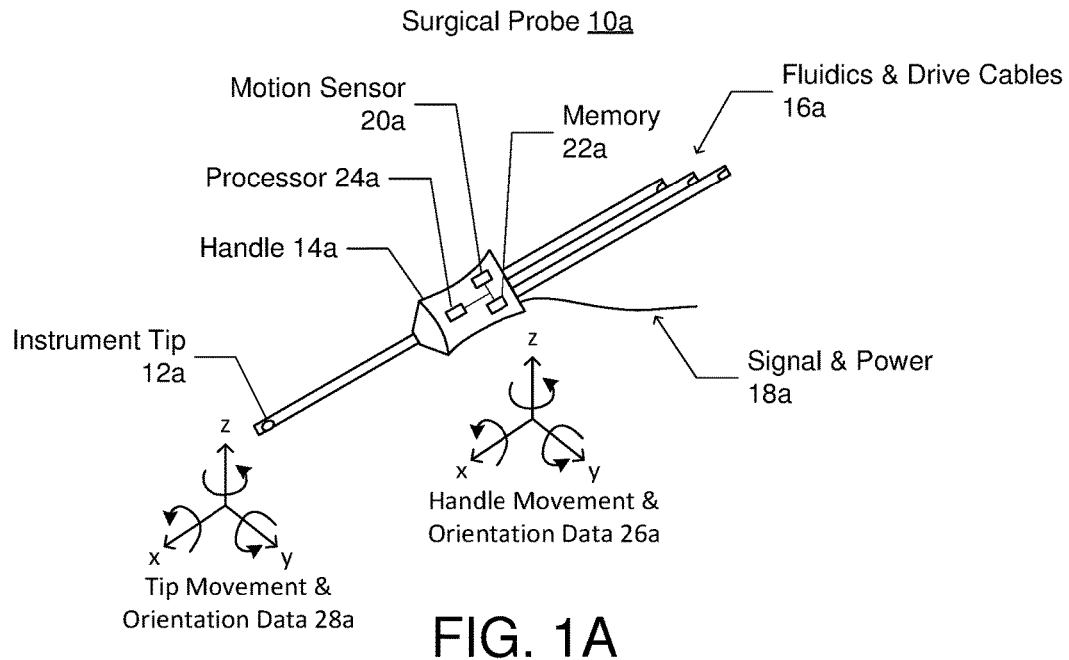
FIGS. 1A and 1B are diagrams illustrating embodiments of a hand-held surgical probe system.
Figure 1B:
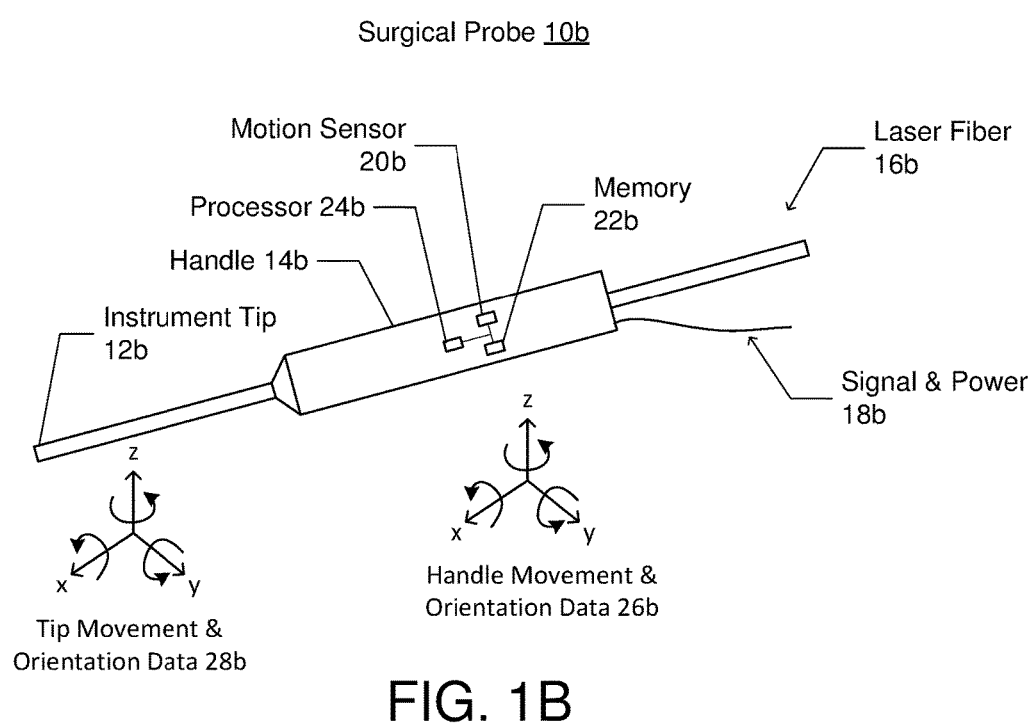

FIGS. 1A and 1B are diagrams illustrating embodiments of a hand-held surgical probe system, where like components have like reference numerals. FIG. 1A shows an embodiment where the surgical probe 10a comprises a vitrectomy probe, which includes an instrument tip 12a connected to a handle 14a, and the handle 14a connected to fluidics and drive cables 16a and a signal and power line 18a. FIG. 1B shows an embodiment where the surgical probe 10b comprises a laser probe, which similarly includes an instrument tip 12b connected to a handle 14b, and the handle 14b connected to a laser fiber 16b and a signal and power line 18b.

According to one aspect of the exemplary embodiments, the surgical probes 10a and 10b are provided with one or more motion sensors 20a and 20b, respectively, located therein that measure handle movement and orientation data 26a and 26b. Handle movement and orientation data 26a and 26b may include measured movement in the form of speed and acceleration along 3 axis (x, y, and z), and measured orientation in the form of rotations around those axes in the form of pitch, yaw, and roll.

Figure 2A:
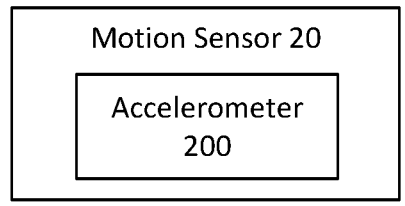
FIG. 2A is a diagram showing that one embodiment, the motion sensor may comprise an accelerometer.
Figure 2B:
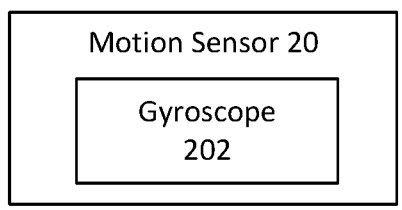
FIG. 2B is a diagram showing that in one embodiment, the motion sensor may comprise a gyroscope.
Figure 2C:
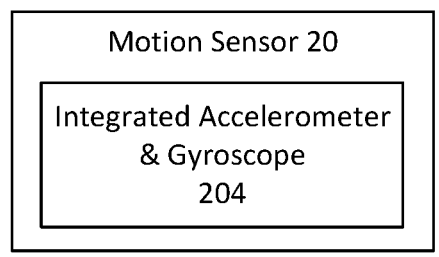
FIG. 2C is a diagram showing that in yet another embodiment, the motion sensor may comprises an integrated accelerometer and gyroscope.

FIG. 2A is a diagram showing that one embodiment, the motion sensor 20a and 20b (collectively referred to as motion sensor 20) may comprise an accelerometer 200, which is a device that measures non-gravitational acceleration. The accelerometer 200 may comprise a two-axis accelerometer or a three-axis accelerometer. FIG. 2B is a diagram showing that in one embodiment, the motion sensor may comprise a gyroscope 202, which is a device that measures the rate of rotation around one or more axis to determine orientation. FIG. 2C is a diagram showing that in yet another embodiment, the motion sensor may comprises an integrated accelerometer and gyroscope 204.

The motion of the surgical probes 10a and 10b during surgery may be a six degree-of-freedom problem: roll, pitch, yaw and XYZ. Therefore, in one embodiment, the surgical probes 10a and 10b may be provided with three orthogonal MEMS (microelectromechanical system) gyros and three orthogonal MEMS accelerometers. The MEMS gyros and accelerometers may be packaged on a single chip and such chips are commercially available.

While the embodiment of FIGS. 1A and 1B show the motion sensor 20 located within the handle of the surgical probe, in an alternative embodiment, the motion sensor 20 may be located near the instrument tip to directly measure instrument tip movement and orientation data 28a and 28b. In yet another embodiment, the surgical probe may include at least one motion sensor located within the handle, and at least one motion sensor located near the instrument tip.

According to a further aspect of the exemplary embodiments, one or more processors 24a and 24b are configured to determine instrument tip movement and orientation data 28a and 28b, based on the handle movement and orientation data 26a and 26b. The processor 24a and 24b may then adjust at least one surgical parameter of the surgical probe 10a and 10b based on the instrument tip movement and orientation data 28a and 28b to affect a predetermined surgical outcome. In the case of a vitrectomy probe, example surgical parameters that may be adjusted include vacuum level, cutrate, stroke, and/or port-opening, and the like. In the case of a laser probe, example surgical parameters may be adjusted include continuous laser power level and pulse laser activation/deactivation.

As used herein below, the surgical probes 10a and 10b may be collectively referred to as surgical probe 10; the memories 22a and 22b may be collectively referred to as memory 22; and the processors 24a and 24b may be collectively referred as processor 24.

In one embodiment, the processor 24 may be located within the surgical probe 10, while in another embodiment the processor 24 may be located remote from the surgical probe 10, such as for example, in a computer or server. In the embodiment where the processor 24 is located within the surgical probe 10, the memory 22 may be coupled to both the motion sensor 14 and the processor 24. The memory 22 may be used to store the software instructions, as well as the data collected by the sensor and the data computed by the processor.

Figure 3A:
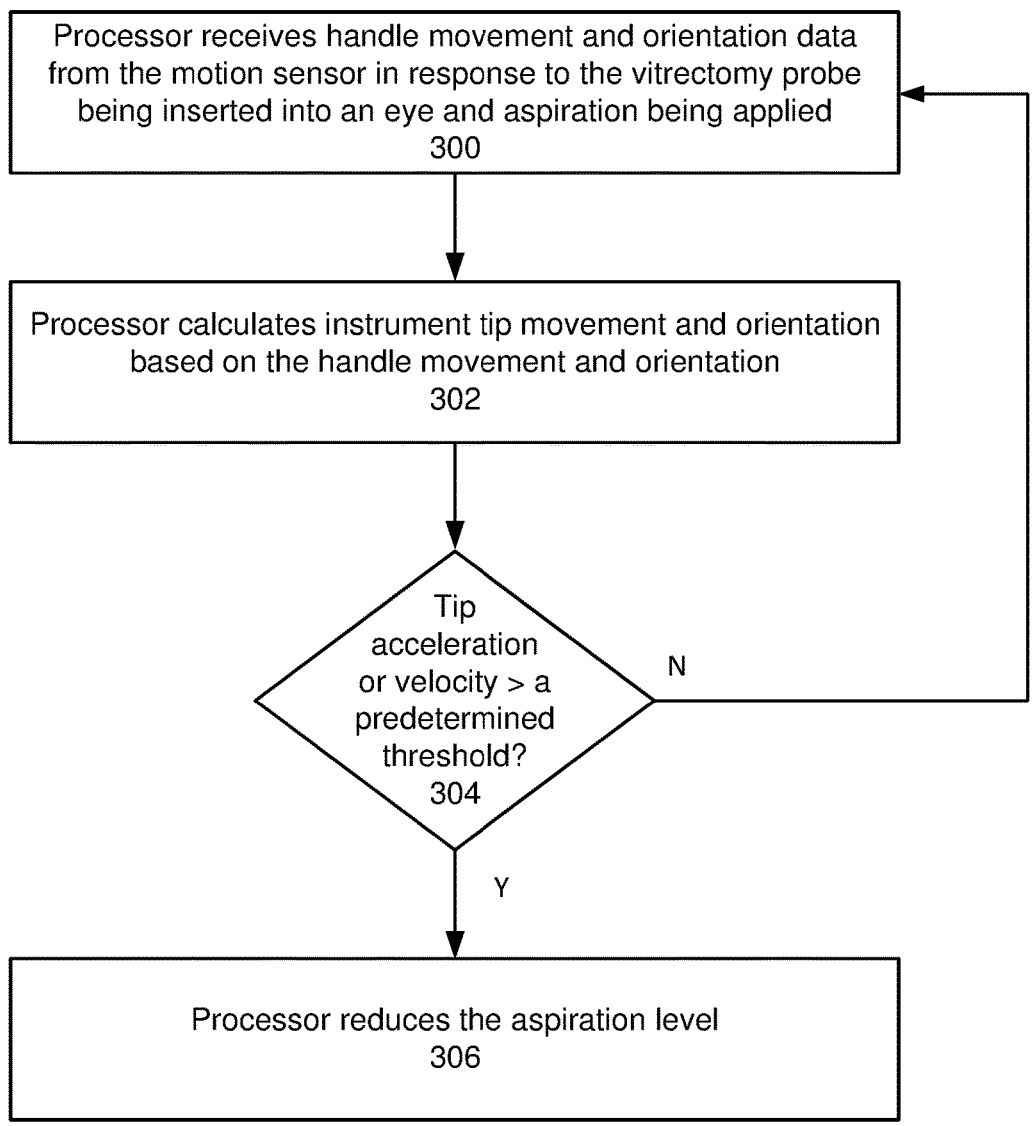
FIG. 3A is a flow diagram illustrating one embodiment of a process performed by a vitrectomy probe having an integrated motion sensor to automatically adjust surgical parameters based on instrument tip movement and orientation.
Figure 3B:
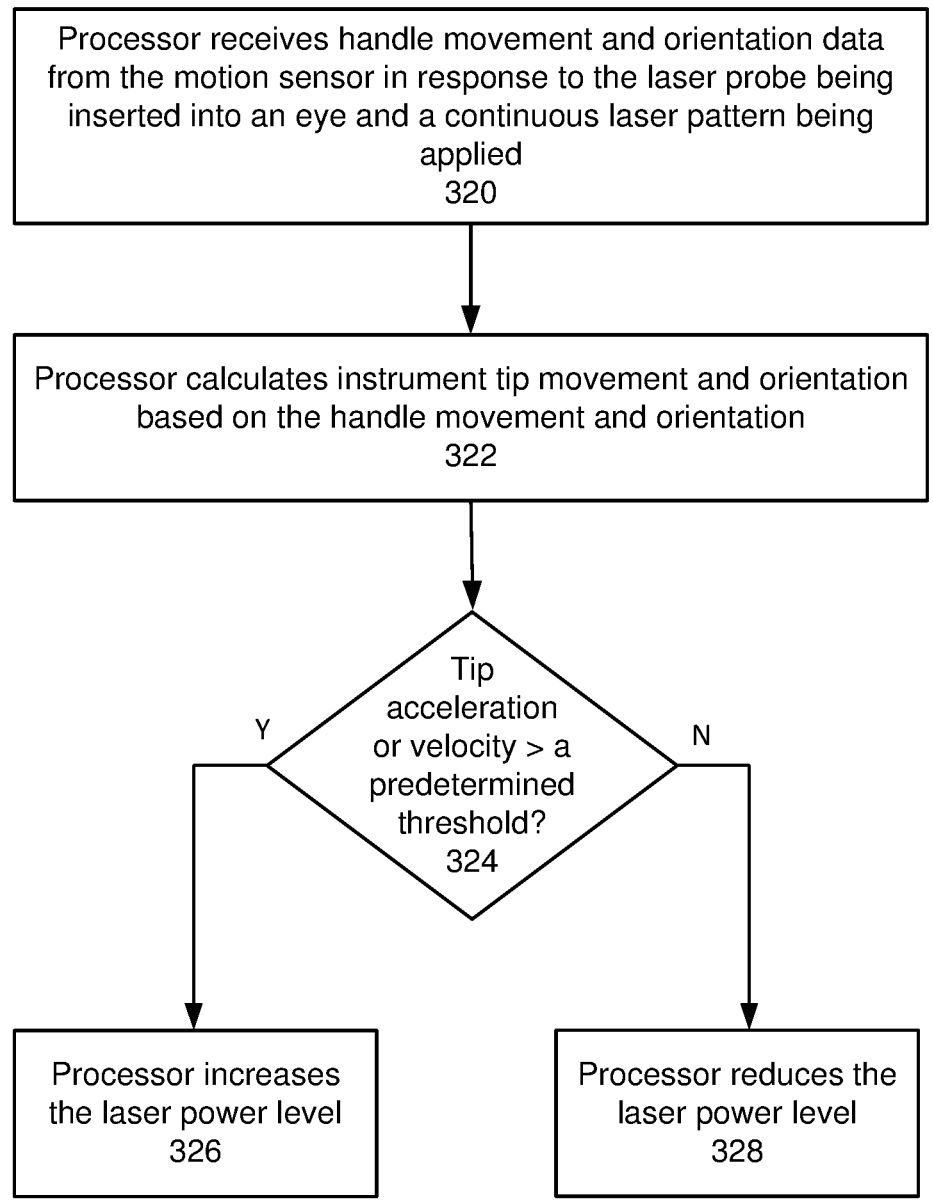
FIG. 3B is a flow diagram illustrating one embodiment of a process performed by a laser probe having an integrated motion sensor to automatically adjust surgical parameters based on instrument tip movement and orientation.

The one or more processors 24 may be configured to execute the instructions stored in the memory 22 to cause and control the process set forth in FIGS. 3A and 3B and described in this disclosure. As used herein, a processor 24 may comprise one or more microprocessors, field-programmable gate arrays (FPGAs), controllers, or any other suitable computing devices or resources. Memory 22 may take the form of volatile or non-volatile memory including, without limitation, magnetic media, optical media, random access memory (RAM), read-only memory (ROM), removable media, or any other suitable memory component. Memory 22 may store instructions for programs and algorithms that, when executed by a processor 24, implement the functionality described herein with respect to any such processor, memory, or component that includes processing functionality.

In one embodiment the processor 24 may be located within the handle 14. In this embodiment, the processor 24 may be provided with a displacement parameter indicating 3-dimensional displacement of the motion sensor 20 away from the instrument tip 12. The processor 24 may then use the displacement parameter in combination with the handle movement and orientation data 26 to derive the instrument tip movement and orientation data 28.

FIG. 3A is a flow diagram illustrating one embodiment of a process performed by a vitrectomy probe having an integrated motion sensor to automatically adjust surgical parameters based on instrument tip movement and orientation. The process may begin by the processor receiving handle movement and orientation data from the motion sensor in response to the vitrectomy probe being inserted into an eye and aspiration being applied (block 300). The processor calculates instrument tip movement and orientation based on the handle movement and orientation (block 302). The processor then determines if instrument tip acceleration and/or or velocity is above a predetermined threshold (block 304). Responsive to the instrument tip acceleration or velocity being above the predetermined threshold, the processor may reduce the aspiration level (block 306). For example, during ophthalmic surgery, the processor may adjust the surgical parameter responsible for closing the aspiration port (e.g., of a vitrectomy probe) or for reducing the vacuum level when fast movements of the instrument tip are detected to reduce iatrogenic damage to the retina. If the instrument tip acceleration or velocity is not above the predetermined threshold, then the process continues with the processor receiving handle movement and orientation from the motion sensor (block 300).

In another embodiment, a laser probe may be augmented with an integrated motion sensor in a similar fashion and the processor may control laser power based on detected velocity of the tip. For example, in continuous laser mode, the processor may increase laser power if faster movement is detected, or decrease the laser power in the case of slower movement to reduce over/under burn, as described below. In laser pulse mode, the processor may activate the laser if no movement or slow movement is detected, and may not activate (or may deactivate) the laser during fast movements to reduce motion blur and spot size.

Use in other instruments is also contemplated. For example, if the surgical probe is a forceps with the incorporated motion sensors and processors described herein, the forceps may automatically open if a fast motion (i.e., acceleration/velocity) above a threshold is detected to reduce unintended tissue trauma during ILM (internal limiting membrane) peeling.

FIG. 3B is a flow diagram illustrating one embodiment of a process performed by a laser probe having an integrated motion sensor to automatically adjust surgical parameters based on instrument tip movement and orientation. The process may begin by the processor receiving handle movement and orientation data from the motion sensor in response to the laser probe being inserted into an eye and a continuous laser pattern being applied (block 320). The processor calculates instrument tip movement and orientation based on the handle movement and orientation (block 322). The processor then determines if instrument tip acceleration and/or or velocity is above a predetermined threshold (block 324). Responsive to the instrument tip acceleration and/or velocity being above the predetermined threshold, the processor increases the laser power level (block 326). Responsive to the instrument tip acceleration and/or or velocity being lower than the predetermined threshold, the processor decreases the laser power level (block 328).

In an alternative embodiment, the surgical parameters of the surgical probe may be adjusted based not only on movement and orientation data, but also on retinal proximity detection. Retinal proximity detection may be performed by an optical or ultrasonic retinal proximity detection sensor that detects proximity or distance between the instrument tip and a retina during surgery.

As further noted below, various embodiments may include a computer-implemented method of automatically adjusting surgical parameters of a surgical probe, the surgical probe comprising an instrument tip, the method comprising: receiving, by a processor, movement and orientation data from at least one motion sensor located within the surgical probe; determining, by the processor, movement and orientation of the instrument tip based on the movement and orientation data; and adjusting, by the processor, at least one surgical parameter of the surgical probe based on the movement and orientation of the instrument tip to affect a predetermined surgical outcome. The processor may be located within a handle of the surgical probe. The processor (e.g., in the handle of the probe) may be provided with a displacement parameter indicating 3-dimensional displacement of the motion sensor away from the instrument tip, and the processor may use the displacement parameter in combination with the movement and orientation data to derive instrument tip movement and orientation data. The surgical probe may include a vitrectomy probe that includes surgical parameters for vacuum level, cutrate, stroke, and port-opening. The surgical probe may include a laser probe with surgical parameters for continuous laser power level and pulse laser activation/deactivation. The at least one surgical parameter may be further adjusted based on retinal proximity detection performed by a retinal proximity detection sensor that detects proximity or distance between the instrument tip and a retina during surgery. In some embodiments, the system may include a non-transitory computer-readable medium containing program instructions for automatically adjusting surgical parameters of a surgical probe, the program instructions for: receiving, by a processor, movement and orientation data from at least one motion sensor located within the surgical probe; determining, by the processor, movement and orientation of the instrument tip based on the movement and orientation data; and adjusting, by the processor, at least one surgical parameter of the surgical probe based on the movement and orientation of the instrument tip to affect a predetermined surgical outcome.

A method and system for a surgical probe having an integrated motion sensor has been disclosed. The present invention has been described in accordance with the embodiments shown, and there could be variations to the embodiments, and any variations would be within the spirit and scope of the present invention. For example, the exemplary embodiment can be implemented using hardware, software, a computer readable medium containing program instructions, or a combination thereof. Accordingly, many modifications may be made by one of ordinary skill in the art without departing from the spirit and scope of the appended claims.

We claim:

1. A surgical probe system, comprising:
    a laser surgical probe having an instrument tip that delivers laser power to an eye;
    at least one motion sensor located within the laser surgical probe that measures movement and orientation data; and
    a processor that:
    determines movement and orientation of the instrument tip based on the movement and orientation data; and
    adjusts the laser power of the surgical probe based on the movement and orientation of the instrument tip to affect a predetermined surgical outcome;
    wherein when the laser probe delivers continuous laser power, the processor:
        increases the laser power if faster movement is detected, or
        decreases the laser power if slower movement is detected.

2. The surgical probe system as in claim 1, wherein the movement and orientation data includes measured movement in a form of speed and acceleration along 3 axis (x, y, and z), and measured orientation in a form of rotations around those axes in a form of pitch, yaw, and roll.

3. The surgical probe system as in claim 1, wherein the at least one motion sensor comprises at least one of an accelerometer and a gyroscope.

4. The surgical probe system as in claim 1, wherein the at least one motion sensor is located within a handle of the surgical probe.

5. The surgical probe system as in claim 1, wherein the at least one motion sensor is located near the instrument tip to directly measure the instrument tip movement and orientation data.

6. The surgical probe system as in claim 1, wherein the at least one motion sensor is located within a handle of the surgical probe, and the surgical probe includes an additional motion sensor located near the instrument tip.

7. The surgical probe system as in claim 1, wherein the processor is located remote from the surgical probe.

8. The surgical probe system as in claim 1, wherein the processor is located within a handle of the surgical probe.

9. The surgical probe system as in claim 8, wherein the processor is provided with a displacement parameter indicating 3-dimensional displacement of the at least one motion sensor away from the instrument tip, and wherein the processor uses the displacement parameter in combination with the movement and orientation data to derive the instrument tip movement and orientation data.

10. The surgical probe system as in claim 1, wherein the laser probe includes surgical parameters for continuous laser power level and pulse laser activation/deactivation.

11. The surgical probe system as in claim 1, wherein at least one surgical parameter is further adjusted by the processor based on retinal proximity detection performed by a retinal proximity detection sensor that detects proximity or distance between the instrument tip and a retina during surgery.

12. A surgical probe system, comprising:
    a laser surgical probe having an instrument tip that delivers laser power to an eye;
    at least one motion sensor located within the laser surgical probe that measures movement and orientation data; and a processor that:
  determines movement and orientation of the instrument tip based on the movement and orientation data; and
  adjusts the laser power of the surgical probe based on the movement and orientation of the instrument tip to affect a predetermined surgical outcome;
  wherein when the laser probe delivers pulsed laser power, the processor:
    activates the laser power if no movement or slow movement is detected, or
    deactivates the laser power if fast movement is detected.

13. The surgical probe system as in claim 12, wherein the movement and orientation data includes measured movement in a form of speed and acceleration along 3 axis (x, y, and z), and measured orientation in a form of rotations around those axes in a form of pitch, yaw, and roll.

14. The surgical probe system as in claim 12, wherein the at least one motion sensor comprises at least one of an accelerometer and a gyroscope.

15. The surgical probe system as in claim 12, wherein the at least one motion sensor is located within a handle of the surgical probe.

16. The surgical probe system as in claim 12, wherein the at least one motion sensor is located near the instrument tip to directly measure the instrument tip movement and orientation data.

17. The surgical probe system as in claim 12, wherein the at least one motion sensor is located within a handle of the surgical probe, and the surgical probe includes an additional motion sensor located near the instrument tip.

18. The surgical probe system as in claim 12, wherein the processor is located remote from the surgical probe.

19. The surgical probe system as in claim 12, wherein the processor is located within a handle of the surgical probe.

20. The surgical probe system as in claim 19, wherein the processor is provided with a displacement parameter indicating 3-dimensional displacement of the at least one motion sensor away from the instrument tip, and wherein the processor uses the displacement parameter in combination with the movement and orientation data to derive instrument tip movement and orientation data.

21. The surgical probe system as in claim 12, wherein the laser probe includes surgical parameters for continuous laser power level and pulse laser activation/deactivation.

22. The surgical probe system as in claim 12, wherein at least one surgical parameter is further adjusted by the processor based on retinal proximity detection performed by a retinal proximity detection sensor that detects proximity or distance between the instrument tip and a retina during surgery.

* * * * *